United States Patent
Jones et al.

(10) Patent No.: US 8,515,988 B2
(45) Date of Patent: Aug. 20, 2013

(54) DATA PAGING WITH A STATELESS SERVICE

(75) Inventors: Jeffrey Dick Jones, Woodinville, WA (US); Gaurav Dinesh Kalmady, Kirkland, WA (US); Sean Patrick Nolan, Bellevue, WA (US); Johnson T. Apacible, Mercer Island, WA (US); Vijay Varadan, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 1086 days.

(21) Appl. No.: 11/860,381

(22) Filed: Sep. 24, 2007

(65) Prior Publication Data

US 2009/0083241 A1    Mar. 26, 2009

(51) Int. Cl.
*G06F 17/30* (2006.01)

(52) U.S. Cl.
CPC ............... *G06F 17/30424* (2013.01)
USPC ............ 707/769; 707/722; 707/761

(58) Field of Classification Search
USPC ............ 707/718, 765, 766, 769, 770, 722, 707/761
See application file for complete search history.

(56) References Cited

U.S. PATENT DOCUMENTS

| | | | |
|---|---|---|---|
| 6,578,068 B1 | 6/2003 | Bowman-Amuah | |
| 6,622,231 B2 | 9/2003 | Kaufman et al. | |
| 6,763,382 B1 * | 7/2004 | Balakrishnan et al. | 709/224 |
| 6,912,534 B2 | 6/2005 | DeBettencourt et al. | |
| 7,203,623 B2 | 4/2007 | Garcea et al. | |
| 2003/0167456 A1 | 9/2003 | Sabharwal | |
| 2005/0165798 A1 | 7/2005 | Cherkauer | |
| 2005/0256834 A1 | 11/2005 | Millington et al. | |
| 2006/0129540 A1 | 6/2006 | Hillis et al. | |
| 2006/0172724 A1 | 8/2006 | Linkert | |
| 2007/0073829 A1 | 3/2007 | Volodarsky et al. | |
| 2007/0156655 A1 * | 7/2007 | Butler et al. | 707/3 |
| 2007/0156842 A1 | 7/2007 | Vermeulen et al. | |
| 2008/0147790 A1 * | 6/2008 | Malaney et al. | 709/203 |

OTHER PUBLICATIONS

C. H. Crawford, et al. Toward an on Demand Service-Oriented Architecture. Aug. 2, 2007. https://www.research.ibm.com/journal/sj/441/crawford.html.
Sriram Anand. Design and Implementation Guidelines for Web Clients. Aug. 2, 2007. http://www.willydev.net/descargas/PartnerAndPractices/WillyDev_DIGWC.pdf.
Design and Implementation Guidelines for Web Clients. http://webservices.sys-con.com/read/104940_2.htm. Last accessed on Aug. 1, 2007.
Creating a Custom Data Paging Solution with IBM WebSphere Portlet Factory. Jun. 21, 2007. http://download.boulder.ibm.com/ibmdl/pub/software/dw/wes/pdf/wpfsamps/CustomDataPaging.pdf.
International Search Report, Written Opinion dated Feb. 25, 2010 for PCT Application Serial No. PCT/US2008/077567, 12 Pages.

* cited by examiner

*Primary Examiner* — Shahid Alam

(57) ABSTRACT

Systems and methods that facilitate data retrieval in a stateless environment by limiting amount of retrievable data associated with a single client request. A retrieval limitation component partially satisfies a query and retrieves an initial batch of information. Moreover, identifications can further be designated to retrieve additional information if so is required. Accordingly, an application requesting data thru a query can initially be supplied with a limited number of data, which subsequently can be followed by additional data items returned as unique identifiers.

12 Claims, 10 Drawing Sheets

DATA PAGING WITH A STATELESS SERVICE

BACKGROUND

The emergence of global communication networks such as the Internet and major cellular networks has precipitated interaction between users and other network entities. Today cellular and IP networks are a principal form of communications, and a central means for interacting with other users for various activities. For example, a computing system interfaced to the Internet, by way of wire or wireless technology, can provide a user with a channel for nearly instantaneous access to a wealth of information from a repository of web sites and servers located around the world. Such a system, as well, allows a user to not only gather information, but also to provide information to disparate sources. As such, online data storing and management has become increasingly popular.

This has led to the development of an increasing number of applications designed to operate over an Internet (and/or World Wide Web) connection. Such applications can include functionality such as tracking personal finances by storing information regarding transactions, for example. Such data can include credit card transactions, bank account transfers, and general information such as account numbers, status, authentication used to gather data from a central bank repository, and the like. Accordingly, network users now have mechanisms for searching and or socializing on virtually any topic of interest. Such vast resource of information can also be an impediment for easily locating information as it continues to grow with no end in sight. This presents a formidable challenge when trying to find the information desired; or to locate other users who have similar points of interest.

An example of a network entity that provides social interaction around common subjects is the social network. Social network theory focuses on the relationships and links between individuals or groups of individuals within the network, rather than the attributes of individuals or entities. Generally, a social network can be described as a structure of nodes that represent individuals or groups of individuals (e.g., organizations). Social networking can also refer to a category of network applications that facilitate connecting friends, business partners, or other entities or groups of entities together.

In general, collaborative social networking websites enable users to create remotely stored profiles including personal data such as age, gender, schools attended, graduating class, places of employment, and the like. Such sites subsequently allow other users to search based on designated criteria and try to locate other users; such as finding a companion with similar interests or locate a long lost friend from high school. According to a further example, banking websites enable users to remotely store information concerning bills to be paid. Accordingly, users can automatically schedule bill payments from their bank account, which is then automatically debited when the payment is scheduled. Such allows simultaneous electronic management of account balancing and bill paying that mitigates manual tasks such as entering checks into the register of their checkbook. However, given the already vast amount of information available on such networks, increasing number of new data sources coming online and the differing types of data being provided, interacting with such services can become cumbersome.

For example, when retrieving large amounts of data from a web-service, inefficiencies can arise due to requesting all data at one time. This retrieval can heavily burden the associated servers or adversely affect operation of the network that transfers that data to requesting clients. Such can further complicate operation in web services (e.g., hosted by a web farm) when no persisted connection exists. This makes it more difficult to obtain consistent results, since a first request can be forwarded to one server, and subsequent requests for more data for the same query may be forwarded to a different server.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

The subject innovation facilitates data retrieval in a stateless environment by limiting an amount of retrievable data associated with a single client request, via a retrieval limitation component that partially satisfies a query and retrieves an initial batch of information—wherein identifications can further be designated to retrieve additional information if so required. The retrieval limitation component can reduce a total amount of data transferred at any given portion of the query, and further include an option component that can supply an option to retrieve more detailed information related to data requested by the query. Accordingly, an application requesting data through a query can initially be supplied with a limited number of data items, which can subsequently be followed by additional data items returned as unique identifiers.

The number of full data items returned can be requested explicitly by the client, and can further be capped at a maximum by the server. When a client desires to supply a request for more data, the range of data and related identifying information can be designated. For example, such designation can be in form of sending unique identifiers for items whose retrieval is desired. This allows the client to retrieve predetermined ranges of data without having to progress through the data linearly.

Hence, an automatic load balancing can be provided between web service servers, when used in a web-farm by servicing multiple independent requests—rather than overloading a single server with a persistent connection, for example. Such can further provide for a client's ability to control amount of data to be retrieved (and when) and in what order. For example, a client can receive items "1 to m" (where m is an integer) in the first request, and can further request items "n to n+k"(where n and k are integers) in a next request. This allows the client to create user experiences similar to paged data, or virtual list views. The application can ask for a snap shot of data, and such application can obtain the actual state of the data that existed when the query was initially issued.

The stateless environment (e.g., stateless web service or web farm where any request can be forwarded to any server) of the subject innovation typically lacks persisted connections (e.g., an active directory that employs a virtual list and maintenance of states on a server), and hence each request to the server can be considered unique and new with no ties to other requests. Accordingly, a client typically assumes responsibility to maintain contextual information to retrieve any additional information.

In a related aspect, the retrieval limitation component can be associated with a query processor as part of the data store, which handles an initial request to obtain results and additional requests for further information or data. According to a further methodology, a type of data desired can be initially designated. Subsequently, a relatively small sample of data can be supplied to the application. By repeatedly asking for a remaining portion of the data, until the required data have been exhausted, such retrieved data can be processed while maintaining contextual information within the application itself for the data.

The subject innovation can further be implemented as part of a mechanism to retrieve data over a federated or heterogeneous health data networks. Moreover, since such sites can themselves be federated, it is oftentimes more expedient to return the information already gathered—as opposed to—waiting for all the sites to respond. As more data comes in, the caller can obtain or retrieve the data by employing the paging mechanism of the subject innovation. Such paging mechanism can also be employed as a throttling mechanism based on the service agreement with third parties. For example, partners who meet a higher bar will be allowed more data to be returned per call, wherein data can be metered both as records counts or by number of bytes returned.

To the accomplishment of the foregoing and related ends, certain illustrative aspects of the claimed subject matter are described herein in connection with the following description and the annexed drawings. These aspects are indicative of various ways in which the subject matter may be practiced, all of which are intended to be within the scope of the claimed subject matter. Other advantages and novel features may become apparent from the following detailed description when considered in conjunction with the drawings.

DETAILED DESCRIPTION

The various aspects of the subject innovation are now described with reference to the annexed drawings, wherein like numerals refer to like or corresponding elements throughout. It should be understood, however, that the drawings and detailed description relating thereto are not intended to limit the claimed subject matter to the particular form disclosed. Rather, the intention is to cover all modifications, equivalents and alternatives falling within the spirit and scope of the claimed subject matter.

Figure 1:
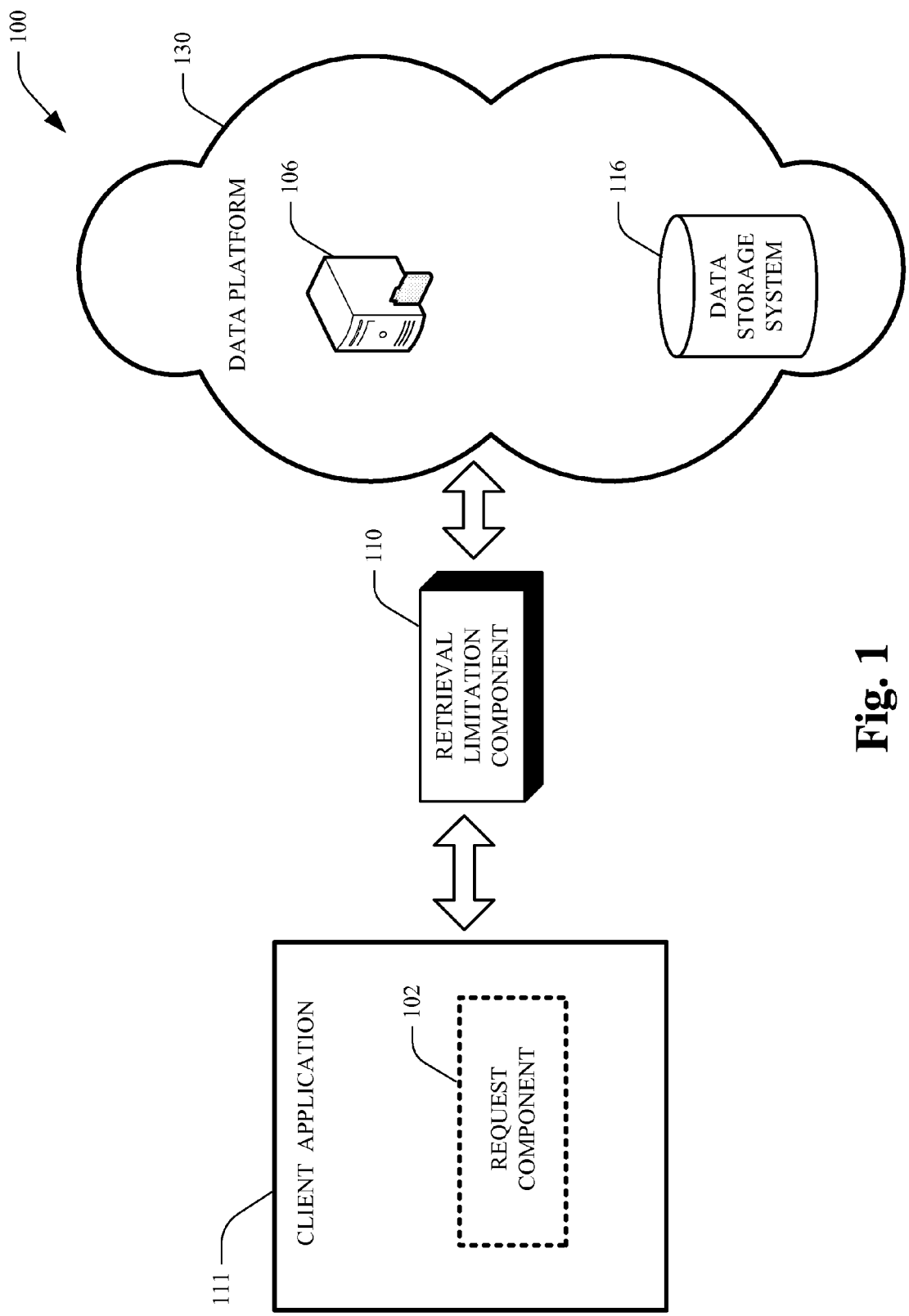
FIG. 1 illustrates a block diagram of a system that limits amount of retrievable data associated with a single client request.

FIG. 1 illustrates a block diagram of a system 100 that provides for a retrieval limitation component 110 in a stateless environment in accordance with an aspect of the subject innovation. Such system 100 facilitates data storage and retrieval (e.g., as part of a health integration network), wherein the retrieval limitation component 110 can limit amount of retrievable data associated with a single client request. Accordingly, the retrieval limitation component 110 can partially satisfy a query and retrieve an initial batch of information—wherein identifications can further be designated to retrieve additional information, if so is required.

The client application 111 can employ a request component 102 that can specify a request for data retrieval, data storage, and the like to an API of the data platform 130. The data platform 130 can interpret the request and query a back-end data component 106 based on the request. The back-end data component 106 can then respond to the API, which can return a result to the request component 102, via the retrieval limitation component 110. The retrieval limitation component 110 can reduce total amount of data transferred at any given portion of the query, and further include an option component (not shown) that can supply an option to retrieve more detailed information related to data requested by the query.

The request component 102 can be any device capable of communicating with the API of the data platform 130. Requests generated by the request component 102 can include: requests for storage of data, retrieval of data, modification of data, and any value-add service to the data, addition of data units, retrieval and application of styles and schemas regarding the format of the data, user interface and layout of the data and the like, for example. Accordingly, the API of the data platform 130 can be employed to interpret requests from the request component 102, and facilitate communication with the back-end data component 106. Moreover, requests forwarded by the request component 102 can be in the form of calls made via XML over hypertext transfer protocol (HTTP), calls made directly to the API, or calls made to a wrapper around the API or a combination thereof. Employing XML typically enables an extensible data model where the structure can change and not require new code, for example.

Moreover, the data storage system 116 can include schematized health related data. For example, the data can be an item including a record corresponding to health related data such as a medical diagnosis; the data can come from many sources including an application used at a doctor's office, or a type of automated diagnosis device such as a home pregnancy test. Moreover, data from such different types of sources can be taken and conform to a single schema that is operable in a centralized health integration network. The data stored in the data storage system 116 can also be related to a new application that desires to register with the health integration network. For instance, the data can include information regarding the name of the application, devices able to access the application, authorization rules for data of the applications, different data types defined and useable by the application; this information can be stored according the schema described herein. Moreover, the data can also be other data related to a user, specifically concerning account information, such as user name, password, and the like. Information such as insurance info, medical history, allergies, and the like can be defined as the individual health records described.

The system 100 relates to stateless environment (e.g., stateless web service or web farm where any request can be forwarded to any server) of the subject innovation typically lacks persisted connections (e.g., lacks an active directory that employs a virtual list and maintenance of states on a server), and hence each request to the server can be considered unique and new with no ties to other requests. Accordingly, a client typically assumes responsibility to maintain contextual information to retrieve any additional information.

Figure 2:
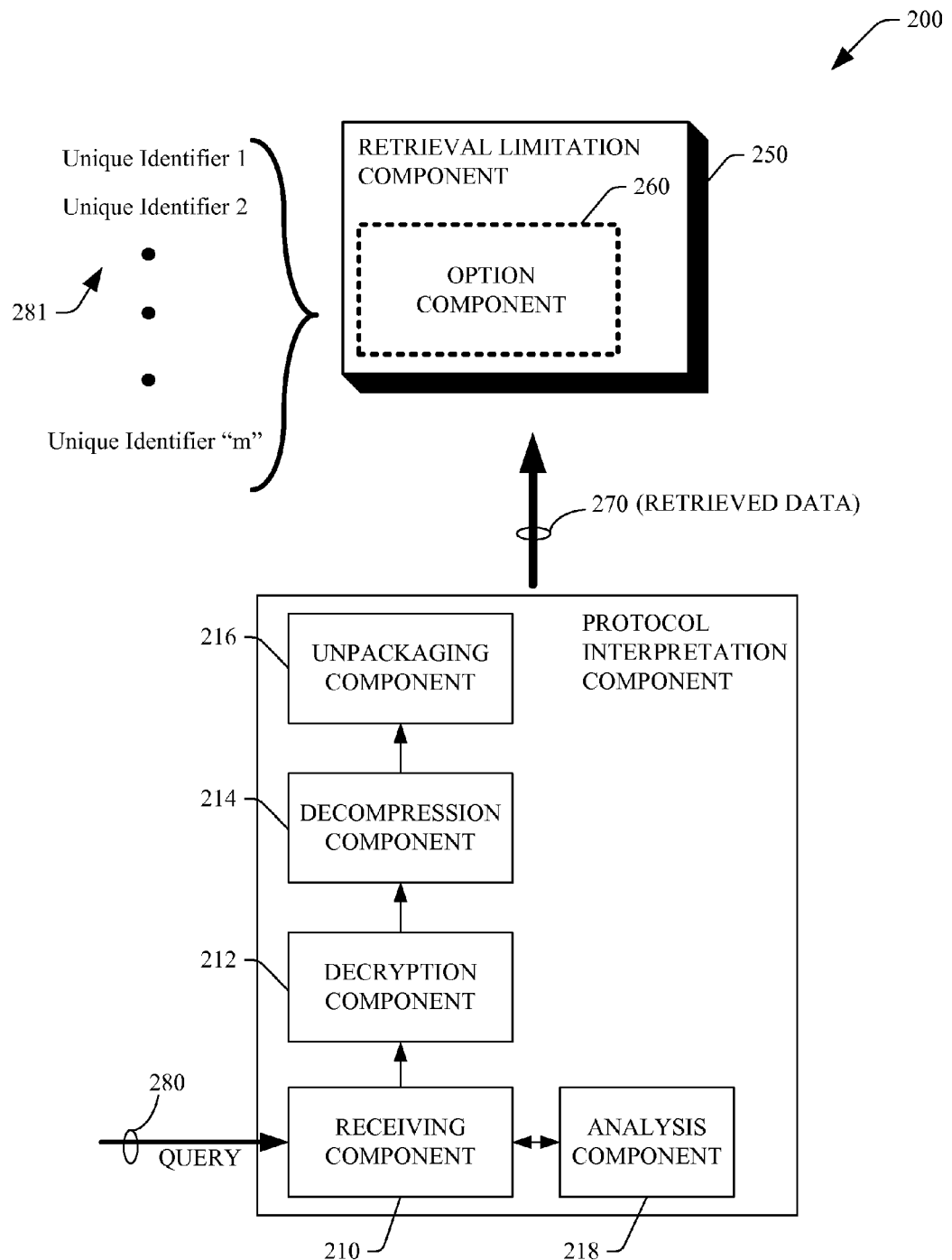
FIG. 2 illustrates a particular block diagram of a retrieval limitation component that can further include an option component in accordance with an aspect of the subject innovation.

FIG. 2 illustrates a retrieval limitation component 250 that includes an option component 260 in accordance with an aspect of the subject innovation. The number of full data items returned can be requested explicitly by the client but can be capped at a maximum by the server. When a client desires to supply a request for more data it sends the unique identifiers 281 for items it desires retrieved. It is to be appreciated that employing unique identifiers for data designation is exemplary in nature and other systems for specifying range of data are well within the realm of the subject innovation. Such system typically allows the client to retrieve certain ranges of data without having to progress through the data linearly.

The application can ask for a snap shot of data, wherein such application can obtain the actual state of the data that existed when the query was initially issued. As further illustrated in FIG. 2, the query 280 can relate to a request made to access personal health related data in a health integration network. A header (not shown) can specify data related to a record_id for which access is requested, as well as actors involved in the request. Once the request is sent, the receiving component 210 can incrementally read the request and employ the analysis component 218 to analyze this information in the header to make preliminary determinations regarding the data that follows and decide whether to continue receiving the request. Additionally, a packaging component (not shown) provides an indication of available compression methods in the header that are supported by a sending application. The receiving application can subsequently employ such compression information in sending any resulting data as retrieved data 270. For example, in the health integration network context, a requesting application can forward the query 280 and specify available methods in a data envelope header according to the protocol specification. Such protocol of the health integration network can receive the request and extract the compression methods. The protocol can determine which method to use upon receiving data to send back from the health integration network to the initial requesting application, as retrieved data 270.

Moreover, the receiving component 210 can incrementally receive the query 280 from a sending component (not shown). Such data can be sent by the sending component as an XML document over an HTTP connection (which can involve an underlying packet based communication medium such TCP/IP), for example. Employing such medium allows packets to be sent over an open communications channel, and thus, the receiving component 210 receives the data in packets (or segments). Accordingly, such data can be incrementally read by the receiving component 210, wherein such component can employ the analysis component 218 to make judgments about the data as it is being received. Accordingly, the receiving component 210 can review the header as it is being sent and send the header to an analysis component 218 to determine information such as workload required to receive and/or process the request, for example. As such, the receiving component 210 and/or analysis component 218 can decide whether to continue receiving the request, and if not, the receiving component 210 can drop the request and close the communications channel. Hence, the receiving component 210 and analysis component 218 can facilitate protection against attacks and security breaches. If the header indicated a relatively large size of a request or a large amount of methods to be accessed, in a health integration network for example, it could deny the request and cease receipt of the data envelope.

Furthermore, the receiving component 210 can read information stored in the header by a packaging component (not shown) such as application specific information, and employ the analysis component 218 to make requests to the application about the data and perhaps deny requests based on such information. For example, in a request to a health integration network, the header can comprise a record_id and an identifier of a person requesting access to the record (and perhaps the type of access requested) and the receiving component 210 can send the information to the analysis component 218, which can leverage the underlying application to make a decision about the requested access before receiving the rest of the request. The decision can be based on setting a trust-level of the message based on the analysis of the record_id and people identifiers and comparing the trust-level to a threshold. Additionally, the information can comprise a previously used authorization token that can be validated by the analysis component 218 while the receiving component 210 continues receiving subsequent data, for example. Moreover, information from different protocol layers (such as the TCP/IP) layer can be used by the analysis component 218 to make decisions about the request. For example, if an IP address has been making malicious requests in the past, an administrator (or artificial intelligence) can specify this to the analysis component 218, and the analysis component 218 can automatically take action upon request from the IP address or notify/suggest the receiving component 210 to do such. It is to be appreciated that the analysis component 218 can also provide the receiving component 210 with the gathered information and allow the receiving component 210 to determine whether to take action. If the determination is made after the data envelope is completely received, the receiving component 210 can compose an error data envelope comprising at least one error code and send the error data envelope back to the requesting application.

Upon receiving at least a portion of the data, the receiving component 210 can send the data to a decryption component 212 that can decrypt the portion of data using a decryption key. The decryption key can be sent in a previous and/or subsequent request, with the current request, known by the system, specified by the system receiving the request (in a subsequent submission, for example), and the like. Upon decrypting the portion of data, the data can be sent to a decompression component 214 as well where at least a portion of the received data can be decompressed according to a compression method. Similarly, to the decryption key, the compression method can be submitted by the receiving application in a previous communication with the sending application, specified in the portion of data received, and/or specified in previous or subsequent submission of data from the sending application. After being decompressed (if necessary), the data can be sent to an unpackaging component 216 that can, for example, remove any data that may be extraneous at this point. For example, once the data has made it through the foregoing components, the header and/or envelope may not be needed anymore and can be separated from the data and discarded by the un-packaging component 216.

The system 200 enables an automatic load balancing between web service servers, when used in a web-farm by servicing multiple independent requests—rather than overloading a single server with a persistent connection, for example. Such can further provide for a client's ability to control when and how much data it retrieves and in what order. For example, a client can receive items 1-100 in the first request but may request items 401-500 in the next request. This allows the client to design user experiences similar to paged data, or virtual list views.

Figure 3:
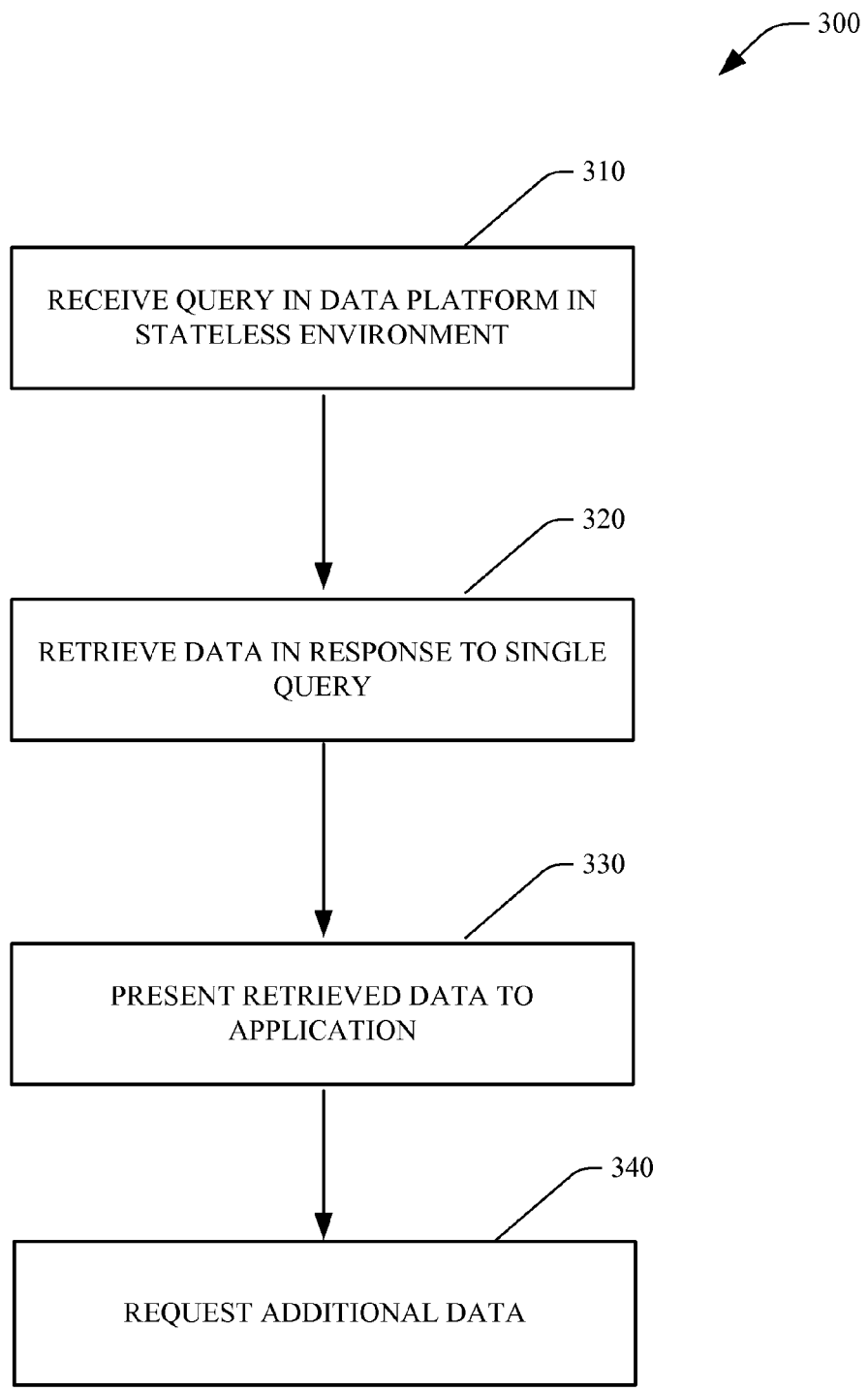
FIG. 3 illustrates a methodology of data retrieval in a stateless system in accordance with an aspect of the subject innovation.

FIG. 3 illustrates a related methodology of data retrieval in a stateless system in accordance with an aspect of the subject innovation. While the exemplary method is illustrated and described herein as a series of blocks representative of various events and/or acts, the subject innovation is not limited by the illustrated ordering of such blocks. For instance, some acts or events may occur in different orders and/or concurrently with other acts or events, apart from the ordering illustrated herein, in accordance with the innovation. In addition, not all illustrated blocks, events or acts, may be required to implement a methodology in accordance with the subject innovation. Moreover, it will be appreciated that the exemplary method and other methods according to the innovation may be implemented in association with the method illustrated and described herein, as well as in association with other systems and apparatus not illustrated or described. Initially and at 310, a query can be issued by an application and forwarded to a data store as part of a data platform in a stateless environment. Such stateless environment (e.g., stateless web service or web farm where any request can be forwarded to any server) of the subject innovation typically lacks persisted connections (e.g., lacks an active directory that employs a virtual list and maintenance of states on a server), and hence each request to the server can be considered unique and new with no ties to other requests. Accordingly, a client typically assumes responsibility to maintain contextual information to retrieve any additional information. Next, and at 320 the single request forwarded to the data store of the data platform can be processed to obtain requested data. At 330, the retrieved data can be supplied to the application. Upon review of such retrieved data, the application can decide if additional retrieval of information is required as related to the single request. Accordingly, the methodology 300 can reduce a total amount of data transferred at any given portion of the query, and supply an option to retrieve more detailed information related to data requested by the query. Accordingly, an application requesting data through a query can initially be supplied with a limited number of data, which can be followed by additional data items returned as unique identifiers.

Figure 4:
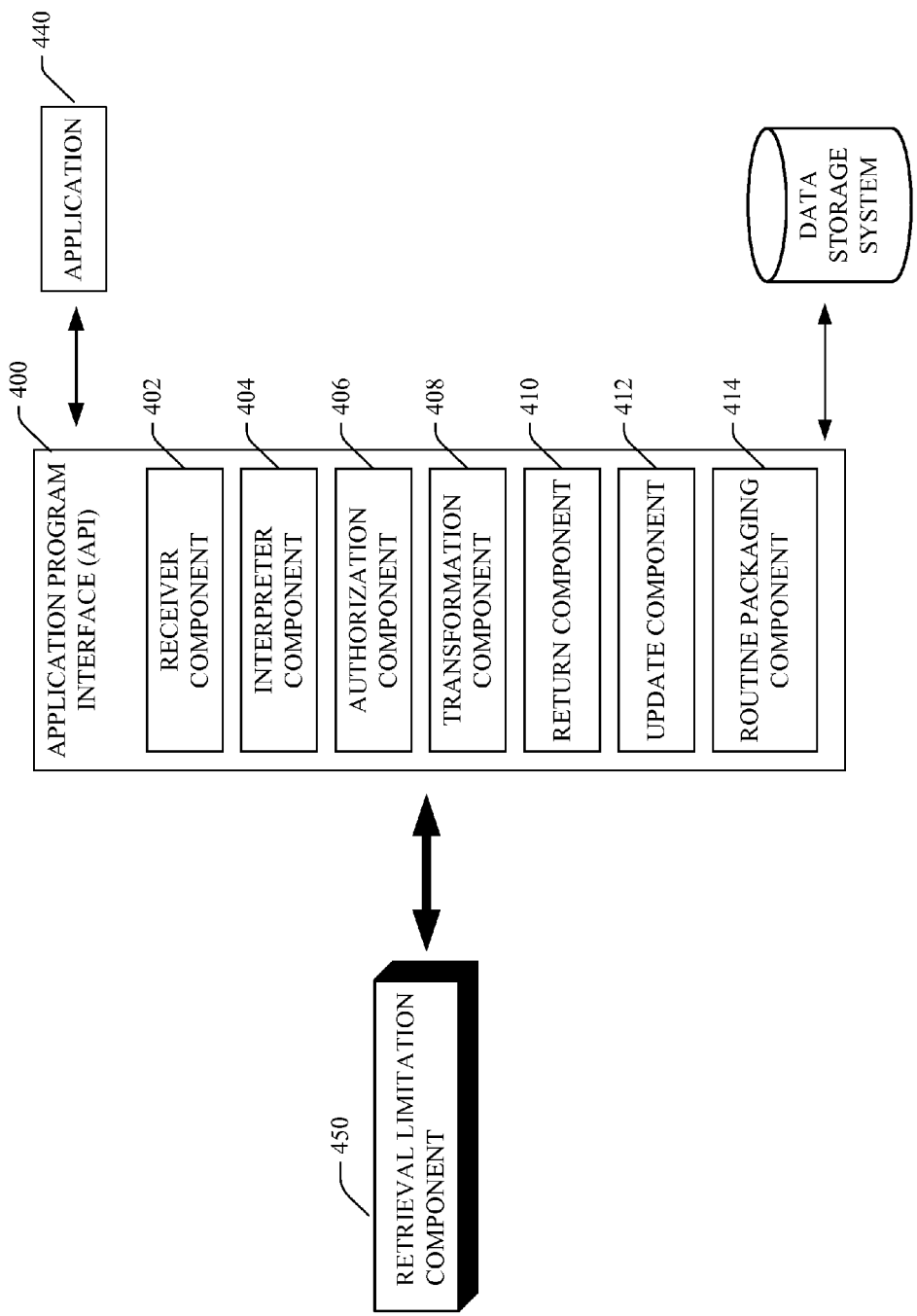
FIG. 4 illustrates a block diagram for a computer implemented system that facilitates data retrieval in accordance with an aspect of the subject innovation.

FIG. 4 illustrates an API 400 that can interact with a retrieval limitation component 450 in accordance with an aspect of the subject innovation. The API 400 has various components to facilitate requests to retrieve, store, modify, or otherwise access data in accordance with the described subject matter. For example, the API 400 can have a receiver component 402 that receives requests for data access, an interpreter component 404 that interprets the request and gathers the desired data and any related data and/or metadata (data about the data). The API 400 can also include an authorization component 406 to apply authorization/authentication rules to the requesting entity to ensure it has sufficient access to make the desired request. The API 400 can have a transformation component 408 that can apply a transformation, translation, style, and/or a schema to the data if desired. The transformation component 408 can also package the resulting data with the appropriate and/or available transformation information so the requesting entity can perform desired transformations. The API 400 can also leverage a return component 410 to send the desired data, as well as any attached data, back to the requesting entity. An update component 412 can enable applications to attach to the API 400, opening a communications channel, and automatically receive updates for information. The API 400 can further provide a routine packaging component 414 for creating intelligent routines to ease use of the API 400.

In a related aspect, when interacting with the API 400, a requesting entity, such as a device, application 440, device running on the application 440, legacy device attached to a system with an application, and the like, can initiate a request for data to the API 400, which is picked up by the receiver component 402. The request can relate to an access personal health and/or fitness related data, for example, such as prescription information. Accordingly, the receiver component 402 can receive the request and sends it to the interpreter component 404. The interpreter component 404 determines the type of request, for example for retrieval of data, storage of data, or modification of data, and determines the record or type being requested. The interpreter component 404 can leverage the authorization component 406 to determine if the requesting entity has sufficient privileges to access the requested data for the type of request presented. For example, a party may not have sufficient access to change or even view a medical diagnosis of their spouse. Authorization rules can be set by many parties, including the person to whom the data directly relates, medical professionals, and the like. If the entity is denied access, the return component 410 can send a resulting error notification (in XML format, for example) back to the requesting entity.

Figure 5:
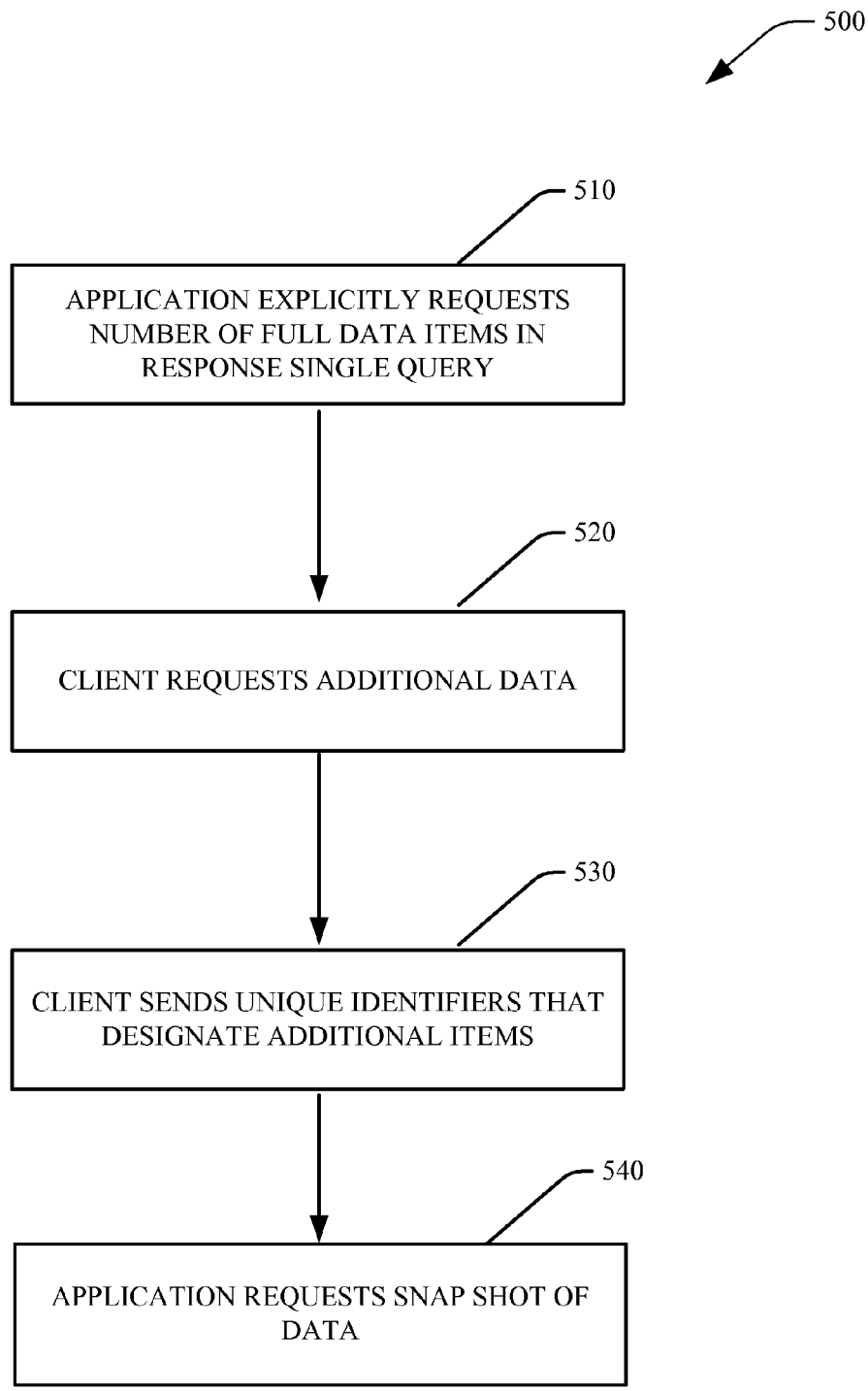
FIG. 5 illustrates a related methodology of requesting a snap shot of data in accordance with an exemplary aspect of the subject innovation.

FIG. 5 illustrates a related methodology 500 for a client to design a user experience in the form of a paged view or a virtual list of views. Initially and at 510 an application explicitly requests the number of full data items returned in response to a single query, which can also be capped at a maximum by the server. At 520, a client desires to supply a request for more data, and at 530 such client can send unique identifiers that designate such additional items it desires to be returned. This allows the client to retrieve certain ranges of data without having to progress through the data linearly. At 540, the application can ask for a snap shot of data, and such application can obtain the actual state of the data that existed when the query was initially issued.

Hence, an automatic load balancing can be provided between web service servers, when used in a web-farm by servicing multiple independent requests—rather than overloading a single server with a persistent connection, for example. Such can further provide for a client's ability to control when and how much data it retrieves and in what order.

Figure 6:
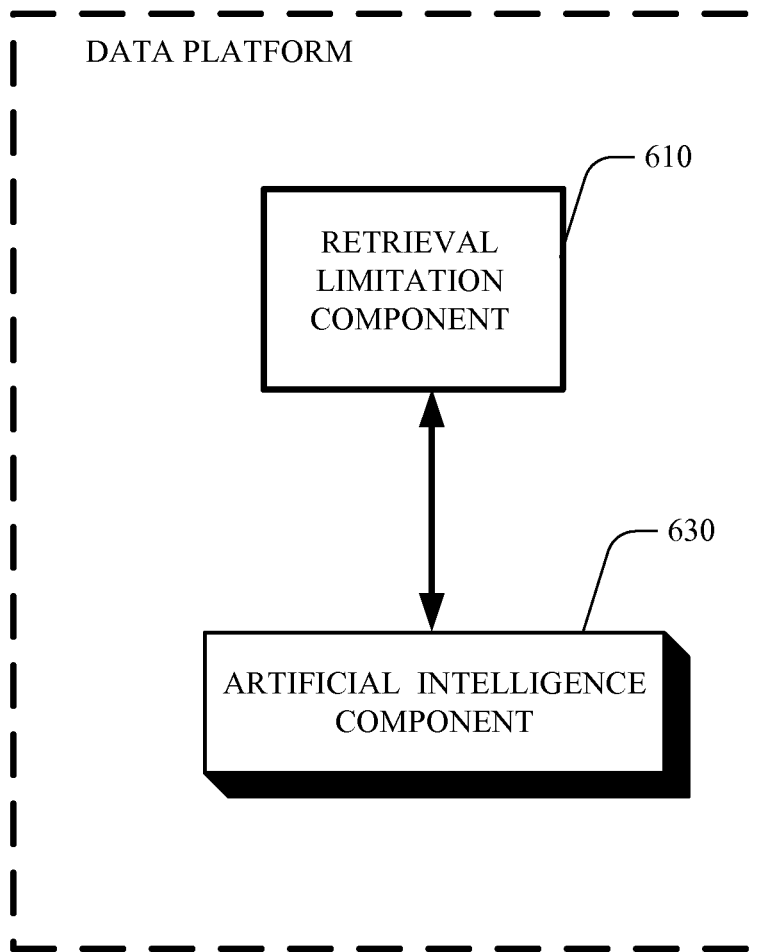
FIG. 6 illustrates an artificial intelligence component that interacts with a retrieval limitation component in accordance with an aspect of the subject innovation.

FIG. 6 illustrates an artificial intelligence component (AI) component 630 that can be employed to facilitate inferring and/or determining when, where, how to generate a limitation on retrieved data in accordance with an aspect of the subject innovation. As used herein, the term "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

The AI component 630 can employ any of a variety of suitable AI-based schemes as described supra in connection with facilitating various aspects of the herein described invention. For example, a process for learning explicitly or implicitly how documents and relationships are to be correlated for generation of invitations can be facilitated via an automatic classification system and process. Classification can employ a probabilistic and/or statistical-based analysis (e.g., factoring into the analysis utilities and costs) to prognose or infer an action that a user desires to be automatically performed. For example, a support vector machine (SVM) classifier can be employed. Other classification approaches include Bayesian networks, decision trees, and probabilistic classification models providing different patterns of independence can be employed. Classification as used herein also is inclusive of statistical regression that is utilized to develop models of priority.

As will be readily appreciated from the subject specification, the subject innovation can employ classifiers that are explicitly trained (e.g., via a generic training data) as well as implicitly trained (e.g., via observing user behavior, receiving extrinsic information) so that the classifier is used to automatically determine according to a predetermined criteria which answer to return to a question. For example, with respect to SVM's that are well understood, SVM's are configured via a learning or training phase within a classifier constructor and feature selection module. A classifier is a function that maps an input attribute vector, $x=(x1, x2, x3, x4, xn)$, to a confidence that the input belongs to a class—that is, $f(x)=confidence(class)$.

Accordingly, the retrieval limitation component 610 can infer the amount of retrieved data and unique identifiers to request additional data, if so required by the application. Moreover, an inference can be made regarding a type of data and proper level of detail desired.

Figure 7:
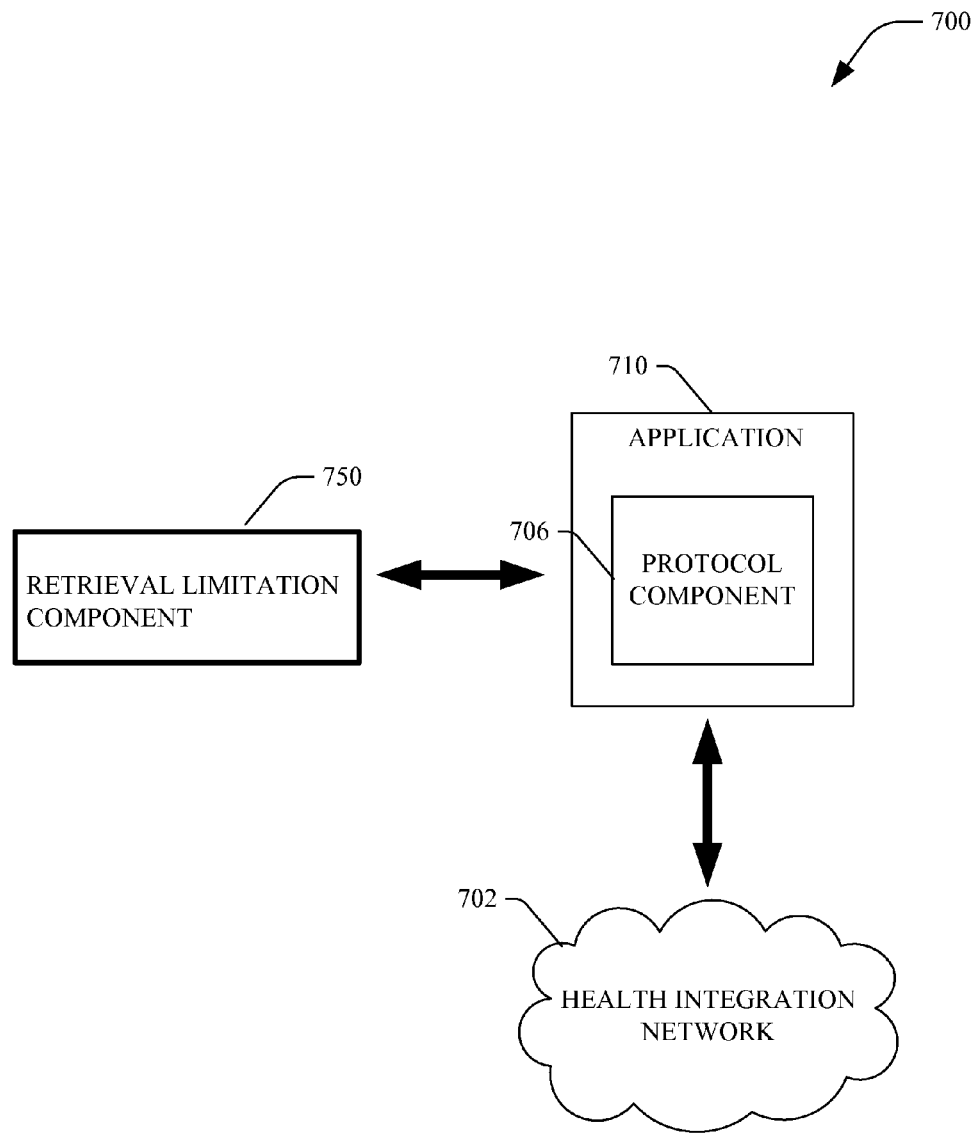
FIG. 7 illustrates a system that facilitates data retrieval in a stateless environment when communicating data to/from a health integration network using a protocol, in accordance with an aspect of the subject innovation.

FIG. 7 illustrates a system 700 that facilitates data retrieval in a stateless environment when communicating data to/from a health integration network using a protocol, and via employing a retrieval limitation component 750. The application 710 can request data from a health integration network 702. The application 710 can employ a protocol component 706 to send requests and receive results. As explained earlier, the protocol component 706 can have respective protocol interpretations components that can employ the components and procedures described earlier to properly conform the data to the protocol specification by using data envelopes and the like. The application 710 can supply requests to the health integration network 702, for example, to retrieve, store, modify, add value to, or otherwise access personal health related data stored in the health integration network 702.

As explained earlier, the protocol component 706 can specify application 710 specific data within a header of a data envelope for the data. The application specific data can include information regarding methods requested, record identifiers for requested data, user ids, authorization tokens, and the like. While incrementally receiving the data envelope, the protocol component 706 can extract information from the header and interact with the health integration network 702 to make preliminary decisions regarding the request for data access. If a decision is made that the request is not desirable, communication can be closed with the application 710 either permanently, temporarily and the like.

For example if a record_id and user_id are provided, the protocol component 708 can leverage the health integration network 702 to ensure the user is authorized in the first place to access the data. Data requested from the application 710 to the health integration network can be to retrieve, store, modify, or otherwise access, for example, data relating to health such as blood pressure readings, insurance information, prescriptions, family history, personal medical history, diagnoses, allergies, X-rays, blood tests, and the like. Additionally, the data can be fitness related, such as exercise routines, exercise goals, diets, virtual expeditions based on exercise routines, competitions, and the like. It is to be appreciated that the protocol component 706 and can be a stand-alone component and/or can at least partially reside within an application or system. For example, the protocol component 706 can be part of the health integration network 702.

Figure 8:
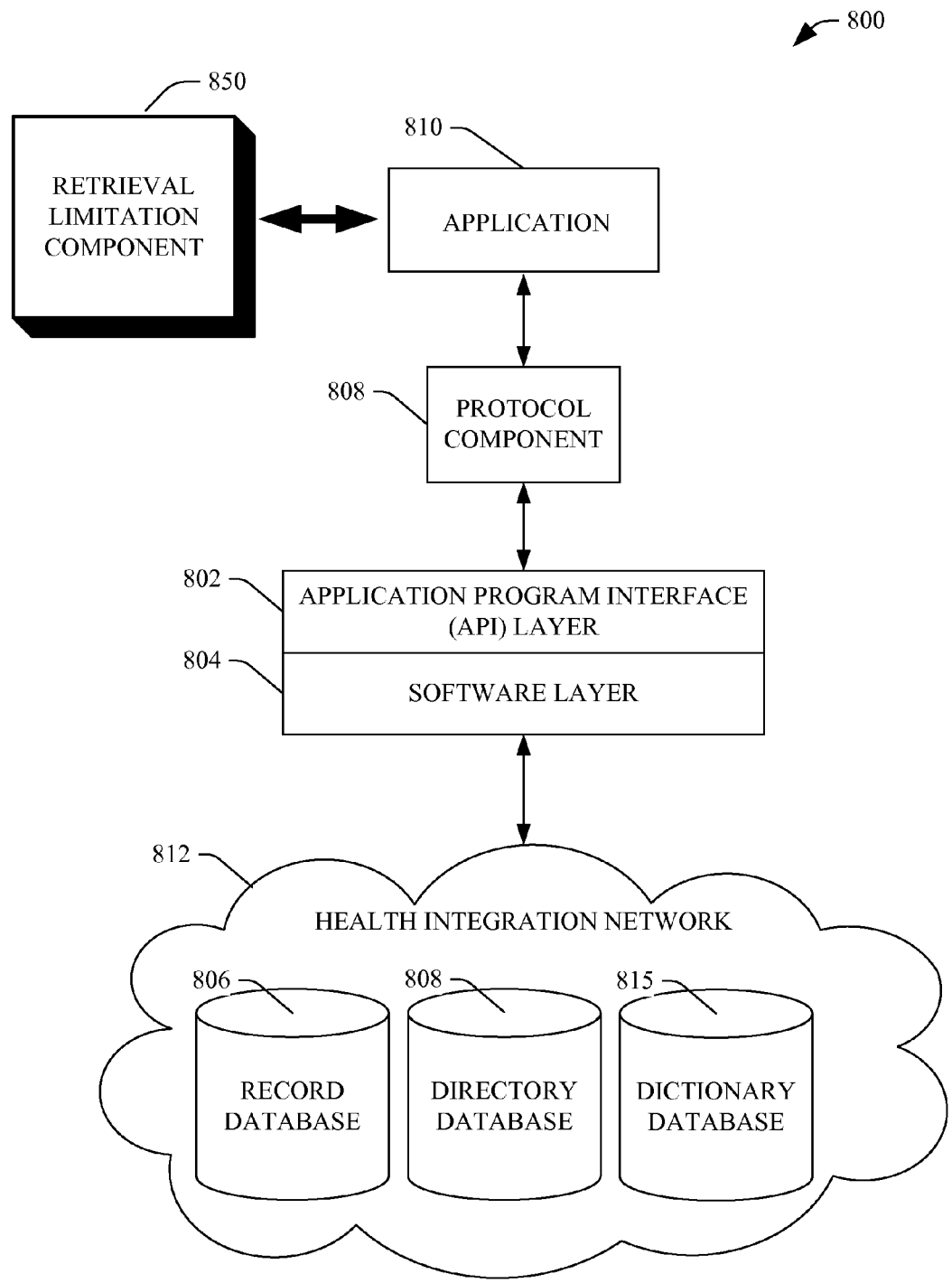
FIG. 8 illustrates a retrieval limitation component that can be employed to facilitate data retrieval in accordance with an aspect of the subject innovation.

FIG. 8 illustrates a further system 800 of the subject innovation, wherein the retrieval limitation component 850 can reduce total amount of data transferred at any given portion of the query, and can further supply an option to retrieve more detailed information related to data requested by the query. Accordingly, an application requesting data thru a query can initially be supplied with a limited number of data, which can be followed by additional data items returned as unique identifiers. The system 800 facilitates access of information to a health integration network. An application 810 can display or specify a limited amount of health related data, with an option to supply more detailed information.

The protocol component 808 can conform request data to a protocol for submission to a remote source such as an API 802. Upon receiving the data content request from protocol component 808, the API 802 can be employed to request and store data within a health integration network 812. It is to be appreciated that the API 802 can synchronously or asynchronously communicate with a plurality of applications 810, through protocol component 808, of similar or different types. The API 802 can also include a software layer 802 to leverage in interpreting and processing the request. The software layer 804 can be separated out as shown, or it can be integrated within the API 802, the health integration network 812, or both. Upon interpreting and processing a request from the application 810, the software layer 804 can access the health integration network 812 for any necessary data or to store necessary data to fulfill the request. The software layer 804 can also provide value-add to the data such as assembling data from the health integration network 812, applying business models or processes in conjunction with data, caching data, and/or applying transformations or additional information to/with the data. It is to be appreciated that there can exist a plurality of APIs 802 and software layers 804 connecting to a centralized health integration network 812, wherein such network can be a single system or distributed across multiple systems, platforms, and the like. The health integration network 812 can comprise a plurality of data stores including a record database 806, a directory database 808, and a dictionary database 810. It is to be appreciated that the health integration network 812 is exemplary in nature and can further comprise other systems and/or layers to facilitate data management and transfer. Furthermore, the databases can be redundant such that multiple versions of the respective databases are available for other APIs and applications and/or a back-up source for other versions of the databases. Additionally, the databases can be logically partitioned among various physical data stores to allow efficient access for highly accessed systems. Moreover, the databases can be hierarchically based, such as XML and/or relationally based. The record database 806 can be highly distributed and comprise personal health related data records for a plurality of users. The records can be of different formats and can comprise any kind of data (single instance, structured or unstructured). Such can include plain data, data and associated type information, self-describing data (by way of associated schemas), data with associated templates (by way of stylesheets for example), data with units (such as data with conversion instructions, binary data), and the like. Moreover, the record database 806 can keep an audit trail of changes made to the records for tracking and restoration purposes. Additionally, any data type or related instances of the foregoing information can be stored in a disparate database such as the dictionary database 810 described infra. The record database 806 can be partitioned, distributed, and/or segmented based on a number of factors including performance, logical grouping of users (e.g. users of the same company, family, and the like).

The directory database 808 can store information such as user account data, which can include user name, authentication credentials, the existence of records for the user, and the like. The directory database 808 can also house information about records themselves including the user to whom they belong, where the record is held (in a distributed record database 806 configuration) authorization rules for the records, and the like. For example, a user can specify that a spouse have access only to the user's fitness related data, and not medical health related data. Accordingly, a user can protect predetermined data while allowing appropriate parties (such as spouse, doctor, insurance company, personal trainer, and the like) or applications/devices (blood pressure machine, pacemaker, fitness watch, and the like) to have access to relevant data. In addition, the directory database 808 can comprise data regarding configuring applications 810 to interact with the health integration network 802. Likewise, applications 810 can be required to register with the health integration network 802, and thus, the application data in the directory database 808 includes the registration information.

The word "exemplary" is used herein to mean serving as an example, instance or illustration. Any aspect or design described herein as "exemplary" is not necessarily to be construed as preferred or advantageous over other aspects or designs. Similarly, examples are provided herein solely for purposes of clarity and understanding and are not meant to limit the subject innovation or portion thereof in any manner. It is to be appreciated that a myriad of additional or alternate examples could have been presented, but have been omitted for purposes of brevity.

As used in this application, the terms "component", "system", are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Furthermore, all or portions of the subject innovation can be implemented as a system, method, apparatus, or article of manufacture using standard programming and/or engineering techniques to produce software, firmware, hardware or any combination thereof to control a computer to implement the disclosed innovation. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Figure 9:
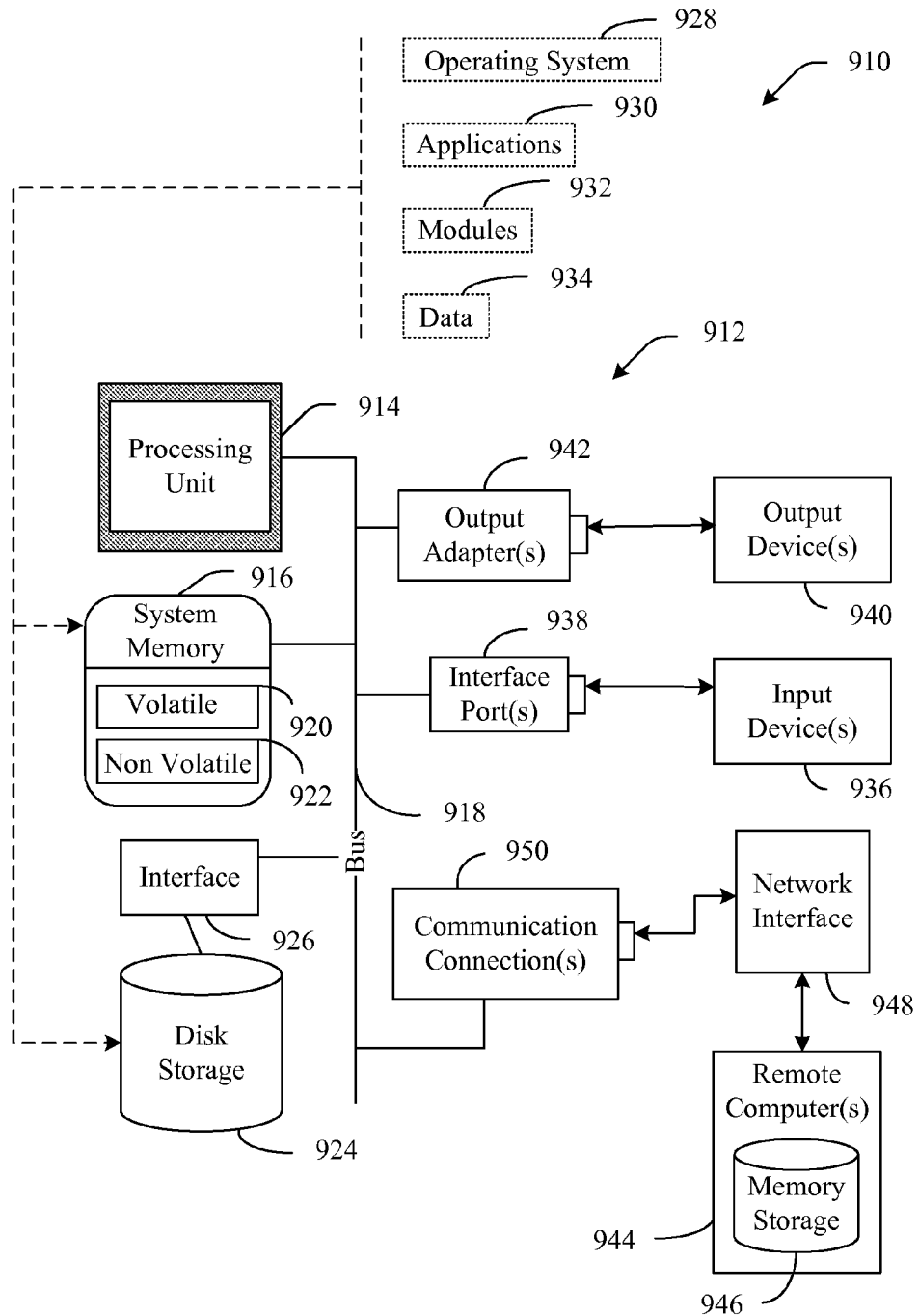
FIG. 9 illustrates an exemplary environment for implementing various aspects of the subject innovation.
Figure 10:
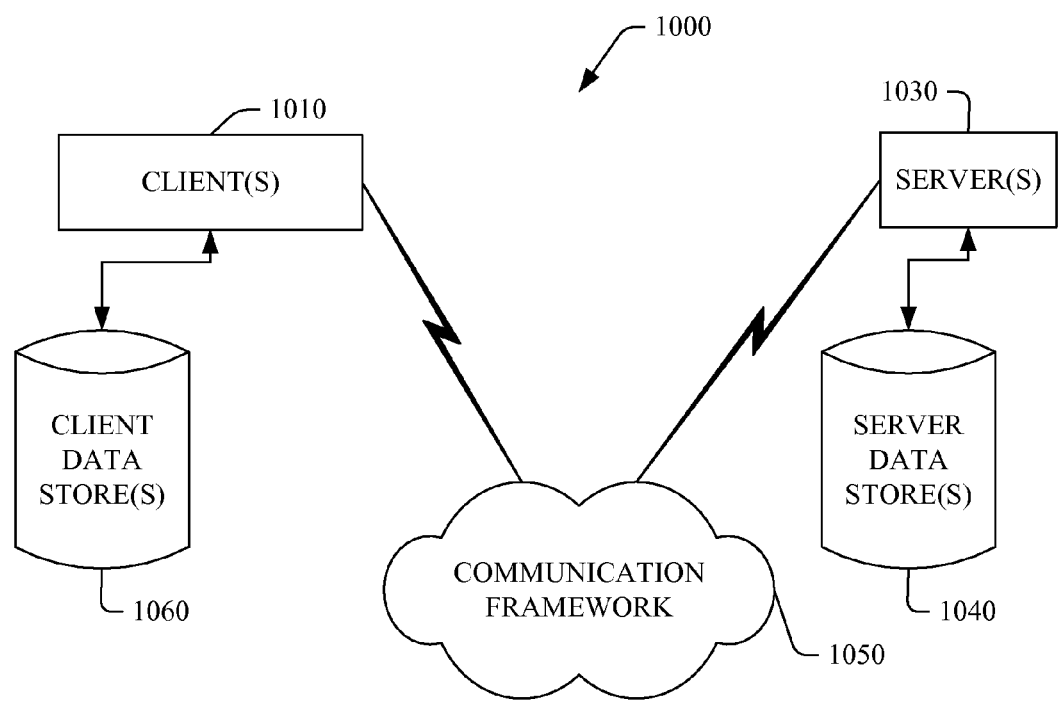
FIG. 10 is a schematic block diagram of a sample computing environment that can be employed for data retrieval according to an aspect of the subject innovation.

In order to provide a context for the various aspects of the disclosed subject matter, FIGS. 9 and 10 as well as the following discussion are intended to provide a brief, general description of a suitable environment in which the various aspects of the disclosed subject matter may be implemented. While the subject matter has been described above in the general context of computer-executable instructions of a computer program that runs on a computer and/or computers, those skilled in the art will recognize that the innovation also may be implemented in combination with other program modules. Generally, program modules include routines, programs, components, data structures, and the like, which perform particular tasks and/or implement particular abstract data types. Moreover, those skilled in the art will appreciate that the innovative methods can be practiced with other computer system configurations, including single-processor or multiprocessor computer systems, mini-computing devices, mainframe computers, as well as personal computers, handheld computing devices (e.g., personal digital assistant (PDA), phone, watch . . . ), microprocessor-based or programmable consumer or industrial electronics, and the like. The illustrated aspects may also be practiced in distributed computing environments where tasks are performed by remote processing devices that are linked through a communications network. However, some, if not all aspects of the innovation can be practiced on stand-alone computers. In a distributed computing environment, program modules may be located in both local and remote memory storage devices.

With reference to FIG. 9, an exemplary environment 910 for implementing various aspects of the subject innovation is described that includes a computer 912. The computer 912 includes a processing unit 914, a system memory 916, and a system bus 918. The system bus 918 couples system components including, but not limited to, the system memory 916 to the processing unit 914. The processing unit 914 can be any of various available processors. Dual microprocessors and other multiprocessor architectures also can be employed as the processing unit 914.

The system bus 918 can be any of several types of bus structure(s) including the memory bus or memory controller, a peripheral bus or external bus, and/or a local bus using any variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

The system memory 916 includes volatile memory 920 and nonvolatile memory 922. The basic input/output system (BIOS), containing the basic routines to transfer information between elements within the computer 912, such as during start-up, is stored in nonvolatile memory 922. By way of illustration, and not limitation, nonvolatile memory 922 can include read only memory (ROM), programmable ROM (PROM), electrically programmable ROM (EPROM), electrically erasable ROM (EEPROM), or flash memory. Volatile memory 920 includes random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

Computer 912 also includes removable/non-removable, volatile/non-volatile computer storage media. FIG. 9 illustrates a disk storage 924, wherein such disk storage 924 includes, but is not limited to, devices like a magnetic disk drive, floppy disk drive, tape drive, Jaz drive, Zip drive, LS-60 drive, flash memory card, or memory stick. In addition, disk storage 924 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 924 to the system bus 918, a removable or non-removable interface is typically used such as interface 926.

It is to be appreciated that FIG. 9 describes software that acts as an intermediary between users and the basic computer resources described in suitable operating environment 910. Such software includes an operating system 928. Operating system 928, which can be stored on disk storage 924, acts to control and allocate resources of the computer system 912. System applications 930 take advantage of the management of resources by operating system 928 through program modules 932 and program data 934 stored either in system memory 916 or on disk storage 924. It is to be appreciated that various components described herein can be implemented with various operating systems or combinations of operating systems.

A user enters commands or information into the computer 912 through input device(s) 936. Input devices 936 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 914 through the system bus 918 via interface port(s) 938. Interface port(s) 938 include, for example, a serial port, a parallel port, a game port, and a universal serial bus (USB). Output device(s) 940 use some of the same type of ports as input device(s) 936. Thus, for example, a USB port may be used to provide input to computer 912, and to output information from computer 912 to an output device 940. Output adapter 942 is provided to illustrate that there are some output devices 940 like monitors, speakers, and printers, among other output devices 940 that require special adapters. The output adapters 942 include, by way of illustration and not limitation, video and sound cards that provide a means of connection between the output device 940 and the system bus 918. It should be noted that other devices and/or systems of devices provide both input and output capabilities such as remote computer(s) 944.

Computer 912 can operate in a networked environment using logical connections to one or more remote computers, such as remote computer(s) 944. The remote computer(s) 944 can be a personal computer, a server, a router, a network PC, a workstation, a microprocessor based appliance, a peer device or other common network node and the like, and typically includes many or all of the elements described relative to computer 912. For purposes of brevity, only a memory storage device 946 is illustrated with remote computer(s) 944. Remote computer(s) 944 is logically connected to computer 912 through a network interface 948 and then physically connected via communication connection 950. Network interface 948 encompasses communication networks such as local-area networks (LAN) and wide-area networks (WAN). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 950 refers to the hardware/software employed to connect the network interface 948 to the bus 918. While communication connection 950 is shown for illustrative clarity inside computer 912, it can also be external to computer 912. The hardware/software necessary for connection to the network interface 948 includes, for exemplary purposes only, internal and external technologies such as, modems including regular telephone grade modems, cable modems and DSL modems, ISDN adapters, and Ethernet cards.

FIG. 10 is a schematic block diagram of a sample-computing environment 1000 that can be employed for implementing data retrieval, in accordance with an aspect of the subject innovation. The system 1000 includes one or more client(s) 1010. The client(s) 1010 can be hardware and/or software (e.g., threads, processes, computing devices). The system 1000 also includes one or more server(s) 1030. The server(s) 1030 can also be hardware and/or software (e.g., threads, processes, computing devices). The servers 1030 can house threads to perform transformations by employing the components described herein, for example. One possible communication between a client 1010 and a server 1030 may be in the form of a data packet adapted to be transmitted between two or more computer processes. The system 1000 includes a communication framework 1050 that can be employed to facilitate communications between the client(s) 1010 and the server(s) 1030. The client(s) 1010 are operatively connected to one or more client data store(s) 1060 that can be employed to store information local to the client(s) 1010. Similarly, the server(s) 1030 are operatively connected to one or more server data store(s) 1040 that can be employed to store information local to the servers 1030.

What has been described above includes various exemplary aspects. It is, of course, not possible to describe every conceivable combination of components or methodologies for purposes of describing these aspects, but one of ordinary skill in the art may recognize that many further combinations and permutations are possible. Accordingly, the aspects described herein are intended to embrace all such alterations, modifications and variations that fall within the spirit and scope of the appended claims.

Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computer-implemented system comprising at least one processor coupled to at least one machine-readable storage medium storing instructions executable by the at least one processor to implement:
    a data platform configured to supply data to a query associated with an application in a stateless environment; and
    a retrieval limitation component configured to make a preliminary determination regarding whether to continue receiving information for the application, the preliminary determination made as the information is received, limit a retrieval of the information for the application based on the preliminary determination so as to reduce a total amount of data transferred at any given portion of the query, and supply at least one identifier option to facilitate a subsequent retrieval of additional data.

2. The computer-implemented system of claim 1, the retrieval limitation component being configured to process the at least one identifier option.

3. The computer-implemented system of claim 1, the stateless environment including a web farm.

4. The computer-implemented system of claim 1, the data platform being configured to supply the data as at least one of a virtual list or paged data.

5. The computer-implemented system of claim 1, the data platform further comprising a query processor.

6. The computer-implemented system of claim 5, further comprising a protocol interpretation component configured to interpret a protocol associated with the data platform.

7. The computer-implemented system of claim 6, the protocol interpretation component comprising an analysis component configured to analyze information associated with a header associated with a query.

8. The computer-implemented system of claim 7, further comprising an application program interface configured to interact with the retrieval limitation component.

9. The computer-implemented system of claim 8, the application program interface comprising an interpreter component configured to determine a type of request by the application.

10. The computer-implemented system of claim 8, further comprising an authorization component configured to determine a privilege associated with access to the data.

11. The computer-implemented system of claim 6, the protocol interpretation component being further configured to extract a compression method from a data header of the request.

12. The computer-implemented system of claim 11, further comprising an artificial intelligence component configured to facilitate data retrieval.

* * * * *